United States Patent [19]

Wilson

[11] Patent Number: 4,707,355

[45] Date of Patent: Nov. 17, 1987

[54] MICROENCAPSULATED INSECTICIDAL BAIT FORMULATIONS AS FUMIGANTS

[75] Inventor: Wilfred W. Wilson, Lake Jackson, Tex.

[73] Assignee: The Dow Chemical Company, Midland, Mich.

[21] Appl. No.: 692,965

[22] Filed: Jan. 22, 1985

[51] Int. Cl.$^4$ .............................................. A01N 25/00
[52] U.S. Cl. ...................................... 424/84; 424/78; 424/406; 424/408; 424/410; 264/4; 264/4.3; 264/4.7
[58] Field of Search .................... 424/17, 20, 78, 84, 424/406, 410, 408; 264/4, 4.3, 4.7

[56] References Cited

U.S. PATENT DOCUMENTS

| | | | |
|---|---|---|---|
| 3,270,100 | 8/1986 | Jolkovski et al. | 264/4 |
| 3,492,380 | 1/1970 | Santo et al. | 264/4 |
| 3,575,882 | 4/1971 | Vandegaer et al. | 264/4.7 |
| 3,577,515 | 5/1971 | Vandegaer | 424/32 |
| 4,076,774 | 2/1978 | Short | 264/4.3 |
| 4,094,970 | 6/1978 | Bekena et al. | 424/78 |
| 4,190,734 | 2/1980 | Dressler | 424/17 |
| 4,285,720 | 8/1981 | Scher | 264/4.7 |
| 4,413,069 | 11/1983 | Marshall | 264/4 |
| 4,557,755 | 12/1985 | Takahashi et al. | 264/4.7 |

FOREIGN PATENT DOCUMENTS 2112345  7/1983  United Kingdom ................ 264/4.7

*Primary Examiner*—Roland W. Griffin
*Attorney, Agent, or Firm*—Gunn, Lee & Jackson

[57] ABSTRACT

A method of manufacturing and the product formed thereby are set forth; the product relates to an encapsulated insecticidal bait which in the preferred and illustrated embodiment has a surrounding shell about a core. The core is formed of a volatile fumigant or ingested toxicant mixed with an insect species attractant food such as soybean oil. The core is enclosed in a shell formed by a two part polycondensate system forming the shell about the core. A first part and a liquid define an interfacial contact around a bead of the first part wherein beads of the core material form droplets in the water. The polycondensate system is defined by the two-part intermediates, where the second part is added to the liquid ratably to encapsulate the droplets.

16 Claims, No Drawings

MICROENCAPSULATED INSECTICIDAL BAIT FORMULATIONS AS FUMIGANTS

BACKGROUND OF THE DISCLOSURE

This disclosure relates to an interfacial encapsulation process for making encapsulated beads particularly suited to enclose a fumigant effective against selected insect species. A typical insect species of concern is the fire ant. Fire ants are difficult to kill with ingested poisons. While ingested poisons may thoroughly decimate foraging worker ants, the use of a chain of tasters in the fire ant colony prevents ingested poison from reaching the queen of the colony, thereby protecting the colony. A particularly valuable volatile insecticidally effective poison includes volatile phosphoric or thiophosphoric acid esters. In addition to operating by ingestion, they provide a fumigant which is airborne, by-passing the tasters. Thus, if the bait is carried into the colony and opened in that closed environment, there is a much greater possibility that the bait will be effective to kill the queen of the colony. The fumigant is is commonly known as DDVP, a fumigant including as one ingredient dimethyl-2, 2-dichlorovinyl phosphate acid ester. There are other fumigant phosphoric or thiophosphoric acid esters which will be collectively referred to also as DDVP. As an example, several such insecticidally effective compounds or mixtures thereof are set forth in U.S. Pat. No. 4,094,970.

DDVP produces a toxic atmosphere for the ants in the colony particularly if the bait can be carried into the colony by foraging ants and is opened in that closed atmosphere. The ants are enticed to open it by incorporation of an attractant food comprising the shell. One suitable attractant food is soybean protein. Hence, the present apparatus contemplates fabrication of a small bead by means of microencapsulation wherein the shell is fabricated with a small measure of soybean protein, and the core is an edible mixed with DDVP. The amount of DDVP is sufficient to be effective in the atmosphere; that is, once the bait has been broken open, DDVP volatilizes sufficiently to have the fatal impact required for colony decimation.

The bead shell is an important factor in preparing the bead of bait material for eventual extermination of a fire ant colony. On the one hand, it should be frangible and broken easily by the insect so that the insect can readily bite through the surrounding shell. On the other hand, the shell must be impervious to water from the exterior, impervious to the core on the interior to prevent DDVP from weeping or saturating the shell material whereby premature fumigation might occur. If this were to happen, premature toxicant exposure might well warn away the foraging ants. Moreover, toxicant exposure might well poison foraging ants before they have the opportunity to deliver the bead into the colony. Thus, it is desirable that the ant finding the bead remove it as a result of foraging; this is a delicate balance wherein the bead must be tough enough to be handled, delivered by machine, and yet should be sufficiently easily opened by insect bite. Moreover, it should be sufficiently free of DDVP which might possibly weep through the wall of the shell and thereby defeat the highly desirable fumigant procedure for insect eradication.

One prior art structure is found in U.S. Pat. No. 4,094,970 setting forth a polyurethane system. Additional references are U.S. Pat. Nos. 3,492,380; 3,575,882; 3,270,100 and 3,577,515. By and large, they generally refer to solid carrier pelletization processes. It is submitted, however, that a quality insecticidal bait must have a toxicant which is enclosed within the bead formed by interfacial encapsulation and there should be an attractant food dissolved in the shell. That is, the attractant food material must in some fashion be in the shell to attract foraging insects. Otherwise, the foraging insects will have no interest in the bead and will ignore it.

The core in the bead is made with DDVP as the fumigant mixed with soybean oil. Separately, the shell ultimately formed should have an attractant such as soybean protein or oil in or on the shell to serve as an attractant. It must either taste or smell good to the foraging insect, sufficiently to cause the insect to carry the bead back to the colony or hive. In this light, it will be understood that the completed bead has the secure, impervious surrounding shell which encapsulates the DDVP. Fumigation does not start until the shell is actually broken open. In the meanwhile, the shell is sufficiently attractive to the foraging insect that it will be carried back to the hive or colony.

Interfacial polycondensation encapsulation is one procedure which enables this to be accomplished. As an example, an interfacial liquid body is defined as having two portions, one being an oil phase which forms droplets in water. The oil phase is added to the water to react with the oil phase at the droplet interface. The polycondensate system is defined by the two parts, one part being the oil phase and the other being the water phase. This method brings the two parts together, thereby achieving bead formation at the droplet interfacial area. With controlled stirring and the addition of either a surfactant or anti-foaming agent, bead size is controlled to form coated beads which are recovered and washed. By this procedure, beads of a selected size are formed and are recovered, washed and thereafter used. The interfacial polycondensate system obtains production of beads in the range of about 1.0 mm or smaller wherein the surrounding shell is impervious to DDVP enclosed therein.

DETAILED DESCRIPTION OF THE PREFERRED METHOD

The present disclosure describes a method of manufacturing a product obtained thereby wherein the product is a two part bead having insecticidal purposes. The bead comprises a central core having a poison such as fumigant successful in confined areas, for instance, in a colony or hive of insects such as fire ants. The core will thus be described first and the surrounding shell for the core which encloses it in an impervious shell (until broken open by the insect) will be described later. The description will describe a method of manufacture for the formation of such encapsulated beads, and certain physical and chemical properties will thereafter be set forth which particularly enable beads prepared in accordance with this disclosure to be used for insect eradication purposes.

The core on the interior of the bead is preferably made with an attractant food such as soybean oil. That is, a food which is attractive to the insect species, which encourages eating by the insect species, is best used. It is used to support a poison such as a fumigant or ingested toxicant described below.

Soybean oil is one suitable attractant food which is used in the core. Alternates include other food oils such as cottonseed oil. They are conveniently available on a relatively low cost, and are generally attractive to a target species. Moreover, this oil is used as a dilution media for the fumigant or toxicant poison. Dimethyl-2,2-dichlorovinyl phosphate and/or other phosphate acid esters are successfully used as a fumigant/toxicant for insect eradication. This is desirable because one major effect is airborne. Decimation of an insect colony is in part dependent on reaching the queen of the colony. The queen, however, is protected or isolated from ingestion of food brought into the hive or colony by foraging insects. Tasters for protection of the health of the queen are interposed between the queen and the foraging insects of the hive or colony. Thus, any poison which operates by ingestion must reach the queen through the tasters. Conversely, the fumigant in the preferred embodiment described below (hereinafter referred to as DDVP) is able to circulate in the closed confines of the hive or colony and thereby evades the intermediate tasters. Greater possibilities of colony extermination are thus obtained. DDVP is also effective as an ingested toxicant.

DDVP is a term applied to the various volatile phosphoric or thiophosphoric acid esters listed below. Some of those which are successful in this function are:
Dimethyl-2,2-dichlorovinyl phosphate
Dimethyl-2,2-dichlorovinyl thiophosphate
Dimethyl-2-chlorovinyl phosphate
Diethyl-2,2-dichlorovinyl phosphate
Diethyl-2-chlorovinyl phosphate
Dipropyl-2-chlorovinyl phosphate
Diisopropyl-2-chlorovinyl phosphate
Dibutyl-2-chlorovinyl phosphate
Diisobutyl-2-chlorovinyl phosphate
Dimethyl-2,2-dibromovinyl phosphate
Dimethyl-2-bromovinyl phosphate
Dimethyl-2-bromo-2-chlorovinyl phosphate
Diethyl-2-bromo-2-chlorovinyl phosphate
Methyl ethyl-2,2-dichlorovinyl phosphate
Dimethyl-1,2-dibromo-2,3-dichloroethyl phosphate
Dimethyl-1,2,2,2-tetrabromoethyl phosphate
Dimethyl-1,2-dibromo-2,2-dichloropropyl phosphate
Dimethyl-2-chloro-1-methylvinyl phosphate
Dimethyl-2-chloro-2-methylvinyl phosphate
Dimethyl-2,2-dichloro-1-methylvinyl phosphate
Dimethyl-2-chloro-1-ethylvinyl phosphate
Dimethyl-2-chloro-2-ethylvinyl phosphate
Dimethyl-2-chloro-1,2-dimethylvinyl phosphate
Diethyl-2-chloro-1-methylvinyl phosphate
Dimethyl-1-chlorovinyl thionophosphate
Dimethyl-2-chloro-1-methylvinyl thionophosphate
Dimethyl-2-chloro-2-methylvinyl thionophosphate The foregoing and other successful insecticidal volatile phosphoric or thiophosphoric acid esters are thus included hereinafter within the definition of DDVP. Either alone or in a mixture, another toxicant is available from Dow Chemical Company and is sometimes sold under the trademark DURSBAN ®. This includes 0,0-diethyl 0-3,5,6-trichloro-2-pyridyl phosphorothioate. The DDVP is mixed with soybean oil. A suitable quantity of the mixture is formed for the fabrication process described below wherein the DDVP has a maximum concentration of up to 5.0%. Depending on the target insect species, DDVP concentration in the mixture of the core material is sufficient up to about 5.0% as a successful insecticidal material. Alternatively, DURSBAN ® insecticide (or a mix with DDVP) is placed in the core to provide optionally a fumigant, an ingested toxicant or both in the core.

The soybean oil solution obtained from the prior step is more in the nature of an oil base material. It becomes part of the oil phase of a two part polycondensate interfacial polymerization system. Recall generally that this disclosure contemplates a method of manufacture involving interfacial polycondensation to form beads.

The shell forming reactants are best described in conjunction with the polycondensate interfacial liquids. The liquid in a container stratifies in the form of oil droplets depending on surface tension of the phase of the constituents. Deionized water is first placed in a container. A suitable anti-foaming agent is added to it. As a second step in the procedure, the oil phase liquid is placed in the same container; it stratifies in the water with stirring to form droplets. The oil phase is a mixture of the soybean oil and DDVP described above along with reactants of a two part polymer or copolymer system. In a preferred version on the present procedure, about 150 grams of the soybean oil/DDVP mixture was mixed with about 24 grams of toluene diisocyanate and 12 grams of sebacoyl chloride. This mixture, after stirring, mixes fairly uniformly. The first added reactant is a precursor for polyurethane polymer fabrication. It is normally soluable in various organic solvents, and is $CH_3 C_6 H_3 (NCO)_2$. Sebacoyl chloride is also generally soluable in hydrocarbons, has the technically correct identification of n-octane-1,8-dicarboxylic acid dichloride. It functions primarily as a reactant in the fabrication of the polymeric shell.

As described at this junction, the oil phase in droplet form floats in the water in the container. As will be understood, the mixing of the core material (food attractant and fumigant) with reactants to form the polymeric shell enables the shell to form and surround the core (having the form of a droplet), and as will be described hereinafter, an attractant food material is placed in the shell. To this end, the remaining reactants for the shell formation are prepared and subsequently mixed in the container. The added reactants are described or labelled as the water phase and are an aqueous solution including about 35 grams of water, about 2 grams of soy protein in the water and 15 grams of diethylene triamine. This water phase is added in the manner described below.

With continued stirring of the water in the container to keep the droplets at proper size, the oil phase is first poured into the container. The oil phase tends to bead, the size of the beads being controlled by the degree of surface tension (keep in mind that an anti-foaming agent is preferably added) and the speed of the stirring. At this juncture, the core material is uniformly distributed in multiple droplets or beads which are specifically but transitorily defined during stirring action; that is, individual beads are formed which also coagulate into larger beads and again break up into smaller beads. This is a rather dynamic situation depending on the stirring and the degree of anti-foaming agent added to the water. Through the use of a funnel extending below the surface of the water in the container, the water phase material is dripped slowly into the water in the container. That is, it is received into the water below the surface. The water phase distributes through the water. As individual beads of the oil phase (defined by surface tension primarily) are brought into contact with the water phase after the addition of the water phase, a polymeric shell is begun around the droplet as a result of the polymeric constituents coaction. The procedure is preferably carried out at approximately room temperature. The stirring is continued for an indefinite period, say, a few hours, to enable the various droplets (resulting from transitory formation by interfacial surface tension) to accumulate a shell formed about them made from the two part polymeric system. After stirring is terminated, the beads can then be removed from the water bath, rinsed repeatedly with deionized water and subsequently dried. The completed product is a small bead having a core with the attractant food and fumigant therein and having a surrounding polymeric shell which protects the bead. Even so, the bead incorporates within the wall of the shell a sufficient amount of food attractant (protein) to entice foraging insects to grasp the bead and remove it to the nest or colony.

The shell is a copolymer around the core. To the extent that unreacted oil phase polymer reactants are in the core, they do not particularly deter insect attraction. The shell is a polyurea, polyamide copolymer cross linked during stirring. The addition of soybean protein to the shell reactants takes advantage of an amine function in the protein to bind the protein in the shell. Thus, the completed shell has sufficient protein (edible and therefore attractive) to cause insects to carry the bead into a nest or colony.

The finished product includes beads in the range of about 1.0 mm and smaller. The thickness of the polymeric shell on the finished beads is in part determined by the duration of stirring the concentration of reactants in the water phase, and the relative quantity of water phase added to the water. In terms of physical properties, the beads obtained by this method of manufacture withstand mechanical handling by the typical types of equipment used for manufacture, packaging, and bait broadcasting. The latter step typically refers to dispersal by machine including tractor pulled equipment or aerial application.

Variations in the percent reactants are noted. For instance, in the oil phase, the amount of DDVP can be increased up to about 5%. Increases beyond this level are generally unnecessary because it is a particularly potent fumigant, and higher percentage levels are not ordinarily needed. As will be understood, the remainder of the core material includes the attractant (soybean oil) which dilutes the fumigant. Moreover, additional dilution is accomplished by the addition of the polymeric reactants in the oil phase. One variation involves use of DURSBAN ® instead of DDVP for the toxicant. This enables manufacture of an insecticidal bead which is primarily an ingested toxicant, or one which is both an ingested toxicant and airborne fumigant. The various listed toxicants can be used singly or mixed; further, the preferred attractant food (soybean oil) can be replaced with oils extracted from other grains such as cottonseed oil.

The ratios provided for the polymer reactants in the oil phase can be varied by about 25% from the examples given above. Significant reduction is believed detrimental in that it will form a skin which is too thin or structurally weak for the completed bead. The water phase reactants can be increased quite significantly; to the degree that there are excess water phase reactants are added to the container, shorter stirring time may result and the excess may simply be left in the container. Generally, it is desirable to provide excess reactant in the water phase. Also, a large container (in comparison with a small container) enables the oil phase droplets of the core material to be more widely dispersed and hence reduces the likelihood of undesirable joinder of partially encased beads.

Consider the following examples. In a stirred flask having about 300 grams of soybean oil therein, DDVP was added and stirred overnight at room temperature to form a toxicant concentration of 1.26%. Using an open top, slick wall container about 4 inches in height and 3 inches in diameter, eighteen imported fire ants of varying maturity were placed in the container. A carefully measured quantity of 0.0098 grams of the 1.26% toxicant/oil solution was placed in an aluminum foil "bucket" or container measuring about 0.5×1.0×0.5 cm, and open at the top. The bucket was suspended about 3 inches above the container. In about fifteen minutes, several ants exhibited tremors, and after one hour several ants were dead while all the remainder were suffering tremors. After about two hours, 6 or 7 ants were dead and all remaining ants were visually observed to be sick. After overnight exposure, all 18 ants were dead.

About 150 grams of the 1.26% toxicant/oil solution was mixed with 24 grams of toluene diisocyanate and 12 grams of sebacoyl chloride, defining the oil phase.

About 600 grams of deionized water in a one liter container having a mechanical stirring device was stirred with two drops of Dow Corning Antifoam 544. The oil phase was poured into the stirring water. After 90 seconds lapsed, the water phase was added slowly by a funnel extending below the surface.

The water phase was a mixture of 35 grams of 6.25% soybean protein (in water) with 15 grams of diethylenetriamine, thoroughly stirred.

After slowly dripping in the water phase, and after about three hours of stirring, beads were recovered from the container. The beads were washed three times in deionized water and then dried at room temperature overnight.

Less than one gram of the beads were placed where foraging imported fire ants of a laboratory colony could collect the beads. A few beads were carried by the ants into the nest. Ants were noticed dead or dying in a few hours, and about 90% of the colony was dead in four days. The colony queen was also dead. Approximate dimension of the bead was in the range of 0.25 to 1.00 mm.

While the foregoing is directed to the preferred embodiment of the present invention, other and further embodiments of the invention may be devised without departing from the basic invention thereof, and the scope thereof is determined by the claims which follow.

What is claimed is:

1. A method of manufacturing an encapsulated insecticidal bait sized for a particular target insect species wherein the bait has the form of a sphere sized for handling by the insect species and which bait is sufficiently rugged to enable machine dispersion and wherein the encapsulation encloses contents thereof until broken open by the insect species, the method comprising the steps of:

(a) forming a first mixture by mixing an oil based insect species attractant food with a poison for the particular insect species and one of a two part system forming a polycondensate:

(b) in a container filled with a liquid not miscible with the first mixture, stirring the liquid while adding the first mixture while controlling the interfacial contact between the liquid and the first mixture by adjustment of surface tension therebetween and causing beads of the first mixture to form in the liquid;

(c) separately gradually adding to the liquid the second of the two part system to cause polycondensate encapsulation of beads of the first mixture wherein the step of adding the second of the two part system is carried out by adding simultaneously therewith an attractant food for the insect species to form an encapsulated bead having the attractant food in the shell formed on the bead; and (d) removing the beads from the container.

2. The method of claim 1 wherein said first mixture includes soybean oil and said poison is a volatile phosphoric or thiophosphoric acid ester which kills the target species by airborne fumigation, and wherein the two part polycondensate system includes an amine for forming a shell about the first mixture including cross-linked polymers or copolymers.

3. The method of claim 1 wherein the liquid in the container is water at room temperature which is initially prepared by the addition of an anti-foaming agent thereto.

4. The method of claim 1 including the step of adjusting the quantity of poison in the first mixture to obtain a concentration of the poison in the finished beads sufficiently strong to fatally fumigate the target insect species on breaking open the beads formed thereby in the presence of the target insect species in a closed colony of the insect species.

5. The insecticidal bait manufactured by the process of claim 1 having a diameter of between about 0.25 and about 1.0 mm.

6. The insecticidal bait made by the process of claim 1 wherein the polycondensate shell has sufficient thickness to enable mechanical handling and is sufficiently impervious to seal against the poison enclosed therein until said shell has been broken to expose the first mixture therein.

7. The product manufactured by the method of claim 1 wherein the product includes up to about 2% by weight volatile phosphoric acid ester mixed in soybean oil, and said shell thereabout includes protein in a quantity sufficient to attract the target insect species.

8. The method of claim 1 wherein said first mixture is comprised of toluene diisocyanate.

9. The method of claim 8 wherein the first mixture is also comprised of sebacoyl chloride.

10. The method of claim 9 wherein said first mixture is reacted with an amine to form a copolymeric shell.

11. The method of claim 10 wherein said oil base food and said one of the two part system have a ratio of about 150:25; and said second part is soluable in the liquid in the container in sufficient quantity to enable stirring to bring a sufficient quantity of said first and second parts together to form the polycondensate bead.

12. The method of claim 11 wherein the beads of the first mixture have a central core and encircling shell; said core being primarily an oil for the insect species, and said poison including volatile phosphoric or thiophosphoric acid esters or 0,0-diethyl 0-3,5,6-trichloro-2-pyridyl phosphorothioate or mixtures thereof.

13. The method of claim 12 wherein the mixture forms the core as a bead defined by surface tension in the liquid.

14. A fire ant poison comprising;
(a) an inner core in a bead including edible fire ant food and DDVP; and
(b) a surrounding shell around said core formed of a polymer or copolymer system mixed with a fire ant attractant food.

15. The poison of claim 14 having the form of an encapsulated bait of diameter of about 0.25 to 1.0 mm, and the attractant food is protein.

16. The poison of claim 15 wherein the fire ant food is soybean oil.

* * * * *